US008653300B2

(12) United States Patent
Fung et al.

(10) Patent No.: US 8,653,300 B2
(45) Date of Patent: Feb. 18, 2014

(54) METHOD FOR MAKING HINDERED PHENOLIC ANTIOXIDANT

(75) Inventors: Dein-Run Fung, Taipei (TW); Jung-Jen Chuang, Taipei (TW); Zhang-Jian Huang, Taipei (TW); Chung-Yu Chen, Taipei (TW)

(73) Assignee: Nan Ya Plastics Corporation, Taipei (TW)

( * ) Notice: Subject to any disclaimer, the term of this patent is extended or adjusted under 35 U.S.C. 154(b) by 602 days.

(21) Appl. No.: 12/461,153

(22) Filed: Aug. 3, 2009

(65) Prior Publication Data

US 2010/0210872 A1    Aug. 19, 2010

(51) Int. Cl.
*C07C 59/00* (2006.01)
*C07C 65/03* (2006.01)

(52) U.S. Cl.
USPC ........................................................ 562/471

(58) Field of Classification Search
None
See application file for complete search history.

(56) References Cited

U.S. PATENT DOCUMENTS

| 4,536,593 | A | * | 8/1985 | Orban et al. | 560/75 |
| 5,710,316 | A | * | 1/1998 | Ruszkay et al. | 560/95 |
| 2002/0120075 | A1 | * | 8/2002 | Yasukohchi et al. | 525/403 |
| 2004/0049007 | A1 | * | 3/2004 | Kodama et al. | 528/403 |

* cited by examiner

*Primary Examiner* — Johann R Richter
*Assistant Examiner* — Jennifer C Sawyer
(74) *Attorney, Agent, or Firm* — Bacon & Thomas, PLLC

(57) ABSTRACT

A method for making a hindered phenolic antioxidant based on Octadecyl 3-(3,5-di-tert-butyl-4-hydroxyphenyl)propionate uses a methanol solution containing alkali metal methoxide as a catalyst solution, wherein the catalyst solution is filtered with a filter device with a filter pore diameter of less than 50 μm to remove insoluble matters therefrom before used in a transesterification process where methyl 3-(3,5-di-tert-butyl-4-hydroxyphenyl)propionate and 1-Octadecanol are taken as reactants to obtain a crude product of Octadecyl 3-(3,5-di-tert-butyl-4-hydroxyphenyl)propionate having high conversion rate and low color, and the crude product further undergoes a purification process for crystallization, filtering and drying to obtain a product of Octadecyl 3-(3,5-di-tert-butyl-4-hydroxyphenyl)propionate having high purity and low color.

3 Claims, No Drawings

METHOD FOR MAKING HINDERED PHENOLIC ANTIOXIDANT

BACKGROUND OF THE PRESENT INVENTION

1. Field of the Present Invention

The present invention relates to a method for making a hindered phenolic antioxidant, and more particularly, to a method for making a hindered phenolic antioxidant based on Octadecyl 3-(3,5-di-tert-butyl-4-hydroxyphenyl)propionate.

2. Description of Related Art

Octadecyl 3-(3,5-di-tert-butyl-4-hydroxyphenyl)propionate is a hindered phenolic antioxidant extensively applied to industries of plastic, synthetic fibers, rubber and petrochemistry as an excellent antioxidative additive.

A conventional method for making Octadecyl 3-(3,5-di-tert-butyl-4-hydroxyphenyl)propionate involves, in the presence of a catalyst, reacting methyl 3-(3,5-di-tert-butyl-4-hydroxyphenyl)propionate with 1-Octadecanol in a transesterification process and, during the transesterification process, continuously removing methanol by-products from the reactants by vaporization or other means, thereby improving the conversion rate in the transesterification process. The crude product Octadecyl 3-(3,5-di-tert-butyl-4-hydroxyphenyl)propionate produced as a result of the transesterification process is then crystallized, filtered and dried to obtain the product of Octadecyl 3-(3,5-di-tert-butyl-4-hydroxyphenyl)propionate. To make Octadecyl 3-(3,5-di-tert-butyl-4-hydroxyphenyl)propionate, the quality and manufacturing cost are subject to the conversion rate in the transesterification process and the color of the product. Thus, it is well recognized that the conversion rate and the color of the crude product obtained through the transesterification process are quite important.

In early days, acid catalysts (such as sulfuric acid and p-toluene sulfo acid) or alkaline catalysts (such as sodium hydroxide and triethylamine) might be used in the transesterification process for making Octadecyl 3-(3,5-di-tert-butyl-4-hydroxyphenyl)propionate. Nevertheless, acid catalysts or alkaline catalysts used in the transesterification process is disadvantageous because of poor performance in reaction, corrosiveness to equipments, and complicated neutralization and washing procedures in order to remove the catalysts after transesterification reaction, thus being inconvenient and difficult to use. To overcome these defects, a transesterification catalyst is made from a neutral organic heavy metal that has good performance in reaction and non-corrosive (such as $(C_4H_9)_2Sn(C_2H_3O_2)_2$). Yet, heavy metal catalysts thus made bring a new problem—the residual heavy metal of Sn may still be left in the product after purification procedures, including crystallization, filtering and drying, have been carried out following the transesterification process.

In recent years, due to people's increasing concern about environmental protection and health care, it is a common request that the finished products of Octadecyl 3-(3,5-di-tert-butyl-4-hydroxyphenyl)propionate shall not contain heavy metal residuals. Hence, it is commonly believed that non-heavy metal is the safer catalyst for transesterification reaction, and that the amount of the catalyst used shall be small enough to spare the complicated procedures for catalyst crystallization, washing and extraction. Alkali metal methoxide (such as lithium methoxide ($CH_3OLi$), sodium methoxide ($CH_3ONa$) and potassium methoxide ($CH_3OK$)) is thus identified as the non-heavy metal catalyst for transesterification reaction because it contains no heavy metal and is efficient in transesterification process even when a small amount of it is used.

Alkali metal methoxide exists in a solid state with a high melting point and is unlikely to be liquefiable. Typically, alkali metal methoxide is dissolved in methanol to form a methanol solution containing alkali metal methoxide and then the methanol solution can be used in transesterification reaction.

Prior arts using alkali metal methoxide as catalysts for transesterification reaction have been taught by U.S. Pat. Nos. 3,784,578 and 5,710,316 for making diallyl phthalate. Therein, U.S. Pat. No. 5,710,316 disclosed that drying the reactant (i.e. an alkyl ester/allylic alcohol mixture) by distillation to less than about 200 ppm water, the transesterification reaction can be achieved by a heating process with the solution of sodium methoxide in methanol/allyl alcohol used in a small amount (less than about 500 ppm based on the amount of the reactant). The methanol by-products are removed overhead by distillation and at last the diallyl phthalate related products, preferably having both high conversion rate and low color, can be obtained.

Similarly, when the method of U.S. Pat. No. 5,710,316 is applied to a process where short linear alcohols are taken as reactants, such as a case where methyl 3-(3,5-di-tert-butyl-4-hydroxyphenyl)propionate and pentaerythritol whose linear chain contains alkyl of 3 carbon atoms are transesterification reactants for making pentaerythritol tetrakis(3-(3,5-di-tert-butyl-4-hydroxyphenyl)propionate), the crude product obtained after the transesterification process is advantageous by its high conversion rate and low color, as affirmed in the patent. After the crude product receives a purification process including crystallization, filtering and drying, the product having high purity and low color can be obtained.

However, when the method of U.S. Pat. No. 5,710,316 is applied to a process where long linear alcohols are taken as reactants, such as a case where methyl 3-(3,5-di-tert-butyl-4-hydroxyphenyl)propionate and 1-Octadecanol whose linear chain contains alkyl of 18 carbon atoms are transesterification reactants for making Octadecyl 3-(3,5-di-tert-butyl-4-hydroxyphenyl)propionate, the crude product of Octadecyl 3-(3,5-di-tert-butyl-4-hydroxyphenyl)propionate after the transesterification process is nevertheless disadvantageous for its low conversion rate and high color. Even after crystallization, filtering and drying, the crude product cannot be turned into a product having high purity and low color. Therefore, the method is unfavorable to mass manufacture.

Through researches and repeated experiments, the inventor of the present invention draws a conclusion that by filtering a methanol solution that contains alkali metal methoxide with a filter device with a filter pore diameter of less than 50 µm so as to remove insoluble matters from the methanol solution before using it as a catalyst in transesterification reaction between methyl 3-(3,5-di-tert-butyl-4-hydroxyphenyl)propionate and 1-Octadecanol, a crude product of Octadecyl 3-(3,5-di-tert-butyl-4-hydroxyphenyl)propionate having high conversion and low color can be obtained. Then by treating the crude product with a purification process for crystallization, filtering and drying, a final product of Octadecyl 3-(3,5-di-tert-butyl-4-hydroxyphenyl)propionate having high purity and low color can be obtained. Hence, given the aforesaid method, Octadecyl 3-(3,5-di-tert-butyl-4-hydroxyphenyl)propionate can be produced by mass production.

SUMMARY OF THE INVENTION

In a transesterification process for making Octadecyl 3-(3,5-di-tert-butyl-4-hydroxyphenyl)propionate where alkali metal methoxide is used as a transesterification catalyst, reactants (i.e. methyl 3-(3,5-di-tert-butyl-4-hydroxyphenyl)propionate and 1-Octadecanol) have to be dried by distillation to less than about 100 ppm of water, so as to allow transesterification reaction in the presence of a small amount (30-150 ppm) of the catalyst. During the transesterification reaction, methanol by-products are removed by vaporization, so as to reduce methanol left in the reactants and speed up production of Octadecyl 3-(3,5-di-tert-butyl-4-hydroxyphenyl)propionate, thereby improving the conversion rate.

Although, in the transesterification process for making Octadecyl 3-(3,5-di-tert-butyl-4-hydroxyphenyl)propionate from methyl 3-(3,5-di-tert-butyl-4-hydroxyphenyl)propionate and 1-Octadecanol, the amount of the catalyst used can be reduced by reducing the moisture of the reactants and the distributive uniformity of the catalyst in the mixed reactants can be improved by using the catalyst in a solution state, the superbase catalyst in the form of the methanol solution containing alkali metal methoxide, if unfiltered, tends to bring coloring matters, poisoning of catalysts, deterioration of catalysts efficiency, and so on, and in turn causes the undesirable crude product to have low conversion rate or high color. Afterward, despite purification treatment for crystallization, filtering and drying, the crude product is unlikely to become a finished product having high purity and low color. Therefore, the importance of the form and amount of the catalyst used in the transesterification process for making Octadecyl 3-(3,5-di-tert-butyl-4-hydroxyphenyl)propionate is evident.

The low conversion rate or high color of the crude product after the transesterification reaction refers to the solid bodies in the crude product being unperceivable to the human eyes or gelled into flocculated solid bodies in the catalyst solution. When the unfiltered catalyst solution is introduced into the heated reactants, the unperceivable solid bodies or the gelled solid bodies tend to form masses due to rapid evaporation of methanol, and the uneven distribution of alkali metal methoxide further leads to localize high concentration of the catalyst in the catalyst solution, destroy the structure of alcohols with long linear chains, such as 1-Octadecanol, and finally bring coloring maters as well as poison the catalyst. Consequently, the crude product of Octadecyl 3-(3,5-di-tert-butyl-4-hydroxyphenyl)propionate obtained through the transesterification process has low conversion rate or high color, thus being undesirable.

To avoid producing the undesirable crude product, the methanol solution containing alkali metal methoxide is preferably filtered with a filter device with a filter pore diameter of less than 50 μm to remove insoluble matters therefrom before being used in the transesterification process. When the filtered catalyst solution is introduced into the reactants and methanol is evaporated due to high heat, the catalyst, namely alkali metal methoxide, as very tiny particles, can be evenly distributed over the reactants. The even distribution of alkali metal methoxide prevents to localize excessively high catalyst concentration and thus prevents to bring coloring maters as well as poison the catalyst during the transesterification reaction, so that the desirable crude product having high yield and low color is then obtained. Afterward, a product of Octadecyl 3-(3,5-di-tert-butyl-4-hydroxyphenyl)propionate having high purity and low color can be easily obtained by performing crystallization, filtering and drying procedures on the crude product.

The primary objective of the present invention is to provide a method for making a hindered phenolic antioxidant based on Octadecyl 3-(3,5-di-tert-butyl-4-hydroxyphenyl)propionate, which method is characterized in that the hindered phenolic antioxidant has 99.0 wt % purity of Octadecyl 3-(3,5-di-tert-butyl-4-hydroxyphenyl)propionate and an APHA color value smaller than or equal to 60. The method comprises steps of:

a) preparing a mixture of methyl 3-(3,5-di-tert-butyl-4-hydroxyphenyl)propionate and 1-Octadecanol having less than 100 ppm water as a reactant mixture;

b) preparing a methanol solution containing alkali metal methoxide as a catalyst solution, filtering insoluble matters from the catalyst solution with a filter device having a filter pore diameter of less than 50 μm, reacting the reactant mixture of Step a), in the presence of the catalyst solution of 30-150 ppm based on a total amount of the reactant mixture, in a reactor at a reaction temperature of 120° C.-240° C. and at a reaction pressure of 10 millibars-1013 millibars for transesterification;

c) during transesterification, continuously removing methanol by-products by vaporization to obtain a crude product based on Octadecyl 3-(3,5-di-tert-butyl-4-hydroxyphenyl)propionate;

d) treating the crude product of Step c) with a purification process including crystallization, drying, and filtering for purification, so as to obtain Octadecyl 3-(3,5-di-tert-butyl-4-hydroxyphenyl)propionate having a purity of 99.0 wt % and an APHA color value less than or equal to 60, for further being used to make hindered phenolic antioxidants.

Wherein alkali metal methoxide used as the catalyst may be lithium methoxide, sodium methoxide or potassium methoxide.

Wherein a concentration of alkali metal methoxide used as the catalyst in the methanol solution is 1-25wt %.

DETAILED DESCRIPTION OF THE PREFERRED EMBODIMENTS

The method of the present invention for making hindered phenolic antioxidant based on Octadecyl 3-(3,5-di-tert-butyl-4-hydroxyphenyl)propionate monomers comprises batch process, semi-batch process and continuous process.

Wherein the typical batch process involves placing a reactant mixture of methyl 3-(3,5-di-tert-butyl-4-hydroxyphenyl)propionate and 1-Octadecanol in a reactor and drying the reactant mixture by vaporization or purge with nitrogen gas to less than about 100 ppm water before a catalyst solution is introduced for transesterification reaction under the reaction temperature of 120° C.-240° C. The catalyst-methanol solution containing alkali metal methoxide is added into the reactant mixture in batch or continuous processing. A use amount of the catalyst solution is 30-150 ppm based on a total amount of the reactant mixture. A reaction pressure starts at 1013.25 millibars (the atmospheric pressure) and gradually reduces to 10 millibars and is maintained at 10 millibars until the transesterification process is finished. During the transesterification process, methanol by-products are continuously removed by vaporization. After the transesterification process, a crude product is obtained and then undergoes a purification process for crystallization, filtering and drying.

The typical continuous process involves continuously feeding a reactant mixture of methyl 3-(3,5-di-tert-butyl-4-hydroxyphenyl)propionate and 1-Octadecanol and a catalyst (methanol solution containing alkali metal methoxide) into a reactor. A crude product (i.e. Octadecyl 3-(3,5-di-tert-butyl-4-hydroxyphenyl)propionate), a by-product (i.e. methanol) and the catalyst (i.e. alkali metal methoxide) are continuously taken out from the reactor and isolated. The crude product after transesterification reaction is then put into a continuous purification process for crystallization, filtering and drying.

To purify the crude product of Octadecyl 3-(3,5-di-tert-butyl-4-hydroxyphenyl)propionate, the methods taught by U.S. Pat. Nos. 3,247,240, 3,642,868, 3,840,585 and 4,085,132 might be applied. The implemented purification process includes crystallization, filtering and drying. A solvent for crystallization may be methanol, ethanol, n-propyl alcohol, isopropyl alcohol, n-butyl alcohol, secondary butyl alcohol, n-hexane, cyclohexane, or pentane.

The catalyst solution containing alkali metal methoxide for the transesterification reaction is prepared by dissolving alkali metal methoxide in methanol to a concentration of 1-25 wt % and filtering the catalyst solution with a filter device with a filter pore diameter of less than 50 μm so as to remove insoluble matters and obtain the filtered catalyst solution for later use. Therein, alkali metal methoxide used as the catalyst may be lithium methoxide, sodium methoxide or potassium methoxide.

The filter device is an airtight container including a filter plate with a filter pore diameter of less than 50 μm. The filter plate may be made of metal, glass, ceramics or plastic and serves to divide the airtight container into two areas for receiving the unfiltered solution and the filtered filtrate, respectively. Pipes for transmission the solution are airtight pies. Before use, the filter device, the container and the pipes shall have water and oxygen completely removed therefrom by, for example, nitrogen gas. The filtering may be conducted by a gravity filtering process or a pressure filtering process. Hereinafter, some examples and comparative examples will be provided for illustrating how the filter pore diameter of the filter device affects the conversion rate, the purity and color of Octadecyl 3-(3,5-di-tert-butyl-4-hydroxyphenyl)propionate. However, it is to be noted that the examples and comparative examples shall be not regarded as limitation to the scope of the present invention.

Physical Tests

Composition of Octadecyl 3-(3,5-di-tert-butyl-4-hydroxyphenyl)propionate is determined by qualitative analysis and quantitative analysis, using a gas chromatography-mass spectrophotometer.

Water content is measured with Kar Fischer Titration Method.

The Pt/Co standard solutions prepared following Step ASDMD-22 80-66 disclosed by American Public Health Association (APHA) as the scale for color measurement. This is also referred to as the APHA Color Standard or well known as the Hazen Platinum Cobalt Scale, whose details are provided in Page 2048 of Standard Method of Chemical Analysis by Wilford W. Scott, $5^{th}$ Edition.

Transesterification Reaction Devices

The devices for transesterification reaction include a three-necked flask reactor (including nitrogen-gas emitting belts) of a capacity of 3 liters, a heating jacket, a thermo indicator, a condenser, a receiver, a decompression pump and a pressure indicator.

Filter Device

The filter devices used here are airtight glass containers with four levels of filer pore diameters, namely 1 μm, 10 μm, 50 μm and 100 μm.

Preparation of Catalyst Solution 38 g of solid lithium methoxide and 342 g of methanol are put into an airtight flask of 0.5 liter and stirred for 2 hours for prompt dissolution so as to obtain a catalyst solution containing lithium methoxide of 10 wt %. Therein, 60 g of the methanol solution is left aside for later use and 320 g of the remaining methanol solution is filtered with the filter devices having the different filer pore diameters.

Nitrogen gas is introduced into each of the filter devices for 10 minutes at a speed of 3 L/minute (based on the volume at 25° C. and 1 atm) for expelling water and oxygen from the devices. Then, the unfiltered methanol solution is divided into four equal parts (each part being 80 g) and filtered respectively by the airtight filter devices having the filter plates with filter pore diameters of 1 μm, 10 μm, 50 μm and 100 μm so as to get filtered methanol solutions for later use.

EXAMPLE 1

306 g of methyl 3-(3,5-di-tert-butyl-4-hydroxyphenyl)propionate (corresponding to 1.05 mole) and 270 g of 1-Octadecanol (corresponding to 1 mole) are used as reactants and put into the reactor, heated to 180° C. till melted, and well stirred. The decompression pump is actuated to reduce the pressure in the reactor down to 80 millibars. Samples of the reactants are taken each 30 minutes and water contents therein are analyzed. When the water content comes to 100 ppm or below, drying of the reactants is finished. Then the decompression pump is turned off and nitrogen gas is introduced into the reactor to return the pressure to the atmospheric pressure. Afterward, the reactor is opened to the atmosphere. Nitrogen gas is introduced into the reactor through the nitrogen-gas emitting belts at the speed of 1 Liter/minute (based on the volume at 25° C. and 1 atm) so as to prevent water and oxygen from entering the reactants.

The catalyst solution filtered by the filter plate of the filter pore diameter of 1 μm is taken as the catalyst. The total amount of the catalyst (lithium methoxide) used is 60 ppm based on the amount of the reactants. A syringe is used to preciously take 0.3456 g of the catalyst solution (concentration 10 wt %) and the catalyst solution is divided into two batches for adding to the reactants, respectively.

When half of the catalyst is added, transesterification reaction between the reactants is started. After 30 minutes, the remaining half of the catalyst is added into the reactants. Vaporization for removing the methanol by-products from the reactor is continuously performed. After 30 more minutes, (entering the second hour), introduction of nitrogen gas is stopped and decompression evaporation is performed to make the pressure from 1013.25 millibars (the atmospheric pressure) gradually reduce to millibars with a speed of 30 millibars/minutes. Afterward, the pressure is held at 10 millibars until the transesterification reaction is completed. The transesterification reaction takes 5 hours to termination when the decompression pump is turned off and nitrogen gas is introduced to the reactor again to return the pressure to the atmospheric pressure. Afterward, the reactor is opened to the atmosphere. Nitrogen gas is introduced into the reactor through the nitrogen-gas emitting belts at the speed of 1 Liter/minute (based on the volume at 25° C. and 1 atm). Samples are then taken for analysis of the conversion rate and color of the crude product of Octadecyl 3-(3,5-di-tert-butyl-4-hydroxyphenyl)propionate. The results of analysis are shown in Table 1.

The crude product of Octadecyl 3-(3,5-di-tert-butyl-4-hydroxyphenyl)propionate is then cooled to 40° C. Then 2000 g of ethanol is put into the reactor which is then heated to 45° C. till the crude product is melted. For crystallization, the temperature of the crude product is reduced to 20° C. at a speed of 0.5° C./minute so as to precipitate crystals. The crystals are then collected by filtering and dried by fluidized bed drying and heated air of 45° C. so as to remove ethanol solvent therefrom. After drying, samples are collected for analysis to measure the purity and APHA color value of the product of Octadecyl 3-(3,5-di-tert-butyl-4-hydroxyphenyl)propionate. The readings are shown in Table 1.

EXAMPLE 2

The method used in the present example is almost identical to that of Example 1 and is repeated except that the catalyst solution filtered by the filter plate with a filter pore diameter of 10 μm.

Samples are taken for analysis to measure the purity and color of the crude product after transesterification reaction and the purity and APHA color value of the product after purification. The readings are shown in Table 1.

EXAMPLE 3

The method used in the present example is almost identical to that of Example 1 and is repeated except that the catalyst solution filtered by the filter plate with a filter pore diameter of 50 μm.

Samples are taken for analysis to measure the purity and color of the crude product after transesterification reaction and the purity and APHA color value of the product after purification. The readings are shown in Table 1.

EXAMPLE 4

The method used in the present example is almost identical to that of Example 3 and is repeated except that the catalyst is filtered methanol solution containing sodium methoxide.

Samples are taken for analysis to measure the purity and color of the crude product after transesterification reaction and the purity and APHA color value of the product after purification. The readings are shown in Table 1.

EXAMPLE 5

The method used in the present example is almost identical to that of Example 3 and is repeated except that the catalyst is filtered methanol solution containing potassium methoxide.

Samples are taken for analysis to measure the purity and color of the crude product after transesterification reaction and the purity and APHA color value of the product after purification. The readings are shown in Table 1.

COMPARATIVE EXAMPLE 1

The method used in the present example is almost identical to that of Example 1 and is repeated except that the catalyst solution filtered by the filter plate with a filter pore diameter of 100 μm.

Samples are taken for analysis to measure the purity and color of the crude product after transesterification reaction and the purity and APHA color value of the product after purification. The readings are shown in Table 1.

COMPARATIVE EXAMPLE 2

The method used in the present example is almost identical to that of Example 1 and is repeated except that the catalyst solution is unfiltered.

Samples are taken for analysis to measure the purity and color of the crude product after transesterification reaction and the purity and APHA color value of the product after purification. The readings are shown in Table 1.

COMPARATIVE EXAMPLE 3

The method used in the present example is almost identical to that of Example 1 and is repeated except that the catalyst is solid lithium methoxide (non-solution).

Samples are taken for analysis to measure the purity and color of the crude product after transesterification reaction and the purity and APHA color value of the product after purification. The readings are shown in Table 1.

Result

By comparing the measurement results of the above embodiments as shown in Table 1, it is concluded that:

1. By using the catalyst solution containing alkali metal methoxide filtered with the filter devices with the filter pore diameters of less than 50 μm to remove insoluble matters therein, the resultant crude product of Octadecyl 3-(3,5-di-tert-butyl-4-hydroxyphenyl)propionate desirably has high yield and low color. After the purification process, the crude product can become a product of Octadecyl 3-(3,5-di-tert-butyl-4-hydroxyphenyl)propionate having high purity and low color.

2. The smaller the filter pore diameter used to filter the catalyst solution containing alkali metal methoxide is, the better filtering effect is, and consequently, the better purity and color the product of Octadecyl 3-(3,5-di-tert-butyl-4-hydroxyphenyl)propionate has.

3. Comparison of the results in Examples 3-5 reveals that catalyst solutions which contain different kinds of alkali metal methoxide, such as lithium methoxide, sodium methoxide, and potassium methoxide, have same effects on the conversion rate and APHA color value of the crude product of Octadecyl 3-(3,5-di-tert-butyl-4-hydroxyphenyl)propionate and the purity and APHA color value of the product of Octadecyl 3-(3,5-di-tert-butyl-4-hydroxyphenyl)propionate after purification.

TABLE 1

Effects of Filter Pore Diameter on Conversion Rate, Purity, and Color

| | Catalyst | Filter Pore Diameter (μm) | Crude Product after Transesterification Reaction | | Product after Purification | |
|---|---|---|---|---|---|---|
| | | | Conversion (%) | APHA Color Value | Purity (wt %) | APHA Color Value |
| Example 1 | Lithium Methoxide in Methanol | 1 | 99.3 | 45 | 99.8 | 30 |
| Example 2 | Lithium Methoxide in Methanol | 10 | 98.5 | 60 | 99.3 | 40 |
| Example 3 | Lithium Methoxide in Methanol | 50 | 98.0 | 90 | 99.0 | 60 |
| Example 4 | Sodium Methoxide in Methanol | 50 | 98.1 | 80 | 99.1 | 50 |

TABLE 1-continued

Effects of Filter Pore Diameter on Conversion Rate, Purity, and Color

| | Catalyst | Filter Pore Diameter (μm) | Crude Product after Transesterification Reaction | | Product after Purification | |
|---|---|---|---|---|---|---|
| | | | Conversion (%) | APHA Color Value | Purity (wt %) | APHA Color Value |
| Example 5 | Potassium Methoxide in Methanol | 50 | 98.0 | 90 | 99.0 | 60 |
| Comp. Example 1 | Lithium Methoxide in Methanol | 100 | 95.0 | 250 (Yellow) | 97.5 | 150 |
| Comp. Example 2 | Lithium Methoxide in Methanol | Unfiltered | 91.8 | 450 (Dark Yellow) | 95.3 | 180 |
| Comp. Example 3 | solid Lithium Methoxide | Solid State | 85.9 | >500 (Dark Brown) | 93.2 | 300 |

What is claimed is:

1. A method for making a hindered phenolic antioxidant, comprising the steps of:
    a) preparing a mixture of methyl 3-(3,5-di-tert-butyl-4-hydroxyphenyl) propionate and 1-octadecanol having less than 100 ppm of water as a reactant mixture;
    b) preparing a methanol solution containing alkali metal methoxide as a catalyst solution, wherein a concentration of the alkali metal methoxide dissolved in the catalyst solution is 1-25 wt % and filtering out insoluble matters unperceivable to human eyes from the catalyst solution with a filter device with a filter pore diameter of less than 50 μm,
    c) reacting the reactant mixture of Step a), in the presence of the filtered catalyst solution of 30-150 ppm based on a total amount of the reactant mixture, in a reactor at a reaction temperature of 120° C.-240° C. and at a reaction pressure of 10 millibars-1013 millibars for transesterification;
    d) removing methanol by-products continuously during transesterification by vaporization to obtain a crude product of octadecanol 3-(3,5-di-tert-butyl-4-hydroxyphenyl) propionate; and
    e) treating the crude product of Step d) with a purification process including crystallization, filtering and drying to obtain a final product of hindered phenolic antioxidant which is octadecyl 3-(3,5-di-tert-butyl-4-hydroxyphenyl) propionate having a purity of 99.0 wt % and an APHA color value less than or equal to 60.

2. A method for making the hindered phenolic antioxidant as claimed in claim 1, wherein the alkali metal methoxide is lithium methoxide, sodium methoxide or potassium methoxide.

3. A method for making the hindered phenolic antioxidant as claimed in claim 1, wherein the filter pore diameter is 1 μm or 10 μm.

* * * * *